United States Patent
Bartko

(10) Patent No.: US 9,856,505 B2
(45) Date of Patent: *Jan. 2, 2018

(54) IDENTIFICATION OF MYCOPLASM CONTAMINATION USING RAMAN SPECTROSCOPY

(71) Applicant: Battelle Memorial Institute, Columbus, OH (US)

(72) Inventor: Andrew P. Bartko, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/082,330

(22) Filed: Mar. 28, 2016

(65) Prior Publication Data

US 2016/0208305 A1    Jul. 21, 2016

Related U.S. Application Data

(63) Continuation of application No. 14/191,887, filed on Feb. 27, 2014, now Pat. No. 9,334,520, which is a (Continued)

(51) Int. Cl.
*G01J 3/44* (2006.01)
*C12Q 1/04* (2006.01)
(Continued)

(52) U.S. Cl.
CPC .............. *C12Q 1/04* (2013.01); *G01N 21/65* (2013.01); *G01N 33/56933* (2013.01); *G01N 21/85* (2013.01); *G01N 2333/30* (2013.01)

(58) Field of Classification Search
CPC ...... G01N 21/31; G01N 21/645; G01N 21/85; G01N 21/6486; G01N 21/65;
(Continued)

(56) References Cited

U.S. PATENT DOCUMENTS 7,532,314 B1    5/2009    Black et al.
7,993,585 B2    8/2011    Black et al.
(Continued)

FOREIGN PATENT DOCUMENTS

JP    2005140794 A    6/2005
JP    2010509601 A    3/2010

OTHER PUBLICATIONS

Notification of Transmittal of the International Search Report and The Written Opinion of the International Searching Authority for PCT Application No. PCT/US2012/052777; dated Nov. 15, 2012; European Patent Office, Rijswijk, Netherlands.
(Continued)

*Primary Examiner* — Sunghee Y Gray
(74) *Attorney, Agent, or Firm* — Thomas E. Lees, LLC

(57) ABSTRACT

A manufacturing method comprises collecting a sample from a cell culture used by a manufacturing application, and controlling a Raman spectrometer to collect a Raman spectrum of a targeted volume within the sample. The method further comprises obtaining reference spectra uniquely associated with a known cell line, which comprise at least two of: spectral measurements of mycoplasma by itself, a contaminated cell line, and a pure cell line. Moreover, the method comprises comparing the reference spectra to the collected spectrum, and identifying whether there is at least one unnatural molecular composition within the collected spectrum based upon the comparison of the reference spectra to the collected spectrum. An indication is provided as to whether mycoplasma is detected in the collected Raman spectrum where at least one unnatural molecular composition is identified within the collected spectrum, and the manufacturing application is stopped where mycoplasma is detected in the collected Raman spectrum.

19 Claims, 4 Drawing Sheets

Related U.S. Application Data continuation of application No. PCT/US2012/052777, filed on Aug. 29, 2012.

(60) Provisional application No. 61/528,849, filed on Aug. 30, 2011.

(51) Int. Cl.
*G01N 33/48* (2006.01)
*A61B 5/00* (2006.01)
*G01N 21/65* (2006.01)
*G01N 33/569* (2006.01)
*G01N 21/85* (2006.01)

(58) Field of Classification Search
CPC ............ G01N 21/6458; G01N 21/658; G01N 2021/656; G01N 2021/6423; G01J 3/10; G01J 3/44; A61B 5/145; A61B 5/14546; A61B 5/411; A61B 5/4833; A61B 5/0836
USPC .................. 356/301; 435/34, 288.7; 702/19; 600/317
See application file for complete search history.

(56) References Cited

U.S. PATENT DOCUMENTS

| | | | |
|---|---|---|---|
| 2003/0037255 A1* | 2/2003 | Yoshino | G01D 9/005 705/51 |
| 2006/0008795 A1* | 1/2006 | Joseph | G01N 33/5005 435/4 |
| 2006/0055923 A1 | 3/2006 | Stewart et al. | |
| 2006/0253261 A1 | 11/2006 | Maier et al. | |
| 2007/0178067 A1 | 8/2007 | Maier et al. | |
| 2007/0258894 A1 | 11/2007 | Melker et al. | |
| 2009/0082220 A1* | 3/2009 | Krause | B82Y 5/00 506/12 |
| 2009/0215052 A1* | 8/2009 | Marc | C12N 1/005 435/6.13 |
| 2010/0241357 A1 | 9/2010 | Chan et al. | |
| 2010/0315628 A1 | 12/2010 | Mertsching et al. | |

OTHER PUBLICATIONS

Notification Concerning Transmittal of International Preliminary Report on Patentability, The International Bureau of WIPO, Geneva, Switzerland and the Written Opinion of the International Searching Authority, European Patent Office, Munich, Germany, for PCT Application No. PCT/US2012/052777, dated Mar. 13, 2014.

Japanese Office Action dated Apr. 26, 2016 for Japanese Patent Application No. 2014-528533; Japanese Patent Office; including an Office Action Summary in English.

Canadian Office Action dated Nov. 1, 2016 for Canadian Patent Application No. 2,839,597; Canadian Patent Office.

* cited by examiner

IDENTIFICATION OF MYCOPLASM CONTAMINATION USING RAMAN SPECTROSCOPY

CROSS REFERENCE TO RELATED APPLICATIONS

This application is a continuation of U.S. patent application Ser. No. 14/191,887, filed Feb. 27, 2014, entitled "IDENTIFICATION OF MYCOPLASM CONTAMINATION IN BIOTECHNOLOGY PRODUCTION USING RAMAN SPECTROSCOPY", now allowed, which is a bypass continuation of International Application No. PCT/US2012/052777, filed Aug. 29, 2012, entitled "IDENTIFICATION OF MYCOPLASM CONTAMINATION IN BIOTECHNOLOGY PRODUCTION USING RAMAN SPECTROSCOPY", which claims the benefit of U.S. Provisional Patent Application Ser. No. 61/528,849, filed Aug. 30, 2011, entitled "IDENTIFICATION OF MYCOPLASM CONTAMINATION IN BIOTECHNOLOGY PRODUCTION USING RAMAN SPECTROSCOPY", the disclosures of which are hereby incorporated by reference.

BACKGROUND

The present disclosure relates to the detection of mycoplasmas, and more particularly to the utilization of Raman Spectroscopy to distinguish and/or otherwise identify unmycoplasma contaminated cells from mycoplasma contaminated cells in biotechnology production.

Numerous modern bioprocess manufacturing applications utilize cell culture systems. For example, in a conventional bioprocess, a cell culture may be used to catalyze biochemical reactions within microorganisms to generate cellular components thereof. After a series of reactions that are contained in a controlled environment, the cell culture chemically changes reactants into end products.

Unfortunately, mycoplasma contamination of cell culture systems is detrimental to such bioprocess manufacturing applications. Mycoplasmas lack a cell wall. Instead, mycoplasma rely upon hosts to maintain their plasma membrane. In this regard, mycoplasmas bind with cell walls of their hosts to obtain nutrients. As such, mycoplasma is extremely small and difficult to detect and filter. Moreover, mycoplasma can cause unexpected deviations in the host cell, e.g., in cell growth, metabolism, function, synthesis, etc. As a result, the cell culture may become contaminated, thus skewing the manufacturing of products from the cell culture and likely destroying the utility of the cell culture.

BRIEF SUMMARY

According to aspects of the present disclosure, a manufacturing method comprises collecting a sample from a cell culture used by a manufacturing application. The method also comprises controlling a Raman spectrometer, by a processor, to collect a Raman spectrum of a targeted volume within the sample so as to collect a Raman spectrum of a single cell of a known cell line of interest. The method further comprises obtaining reference spectra uniquely associated with the known cell line. The reference spectra comprise at least two of spectral measurements of mycoplasma by itself, a contaminated cell line, and a pure cell line. Moreover, the method comprises comparing, using a processing device, the reference spectra to the collected spectrum, and identifying whether there is at least one unnatural molecular composition within the collected spectrum based upon the comparison of the reference spectra to the collected spectrum. In this regard, the method yet further comprises providing an indication as to whether mycoplasma is detected in the collected Raman spectrum where at least one unnatural molecular composition is identified within the collected spectrum, and stopping the manufacturing application where mycoplasma is detected in the collected Raman spectrum.

For example, the targeted volume may be identified as a potential host volume if the targeted volume is identified as a belonging to a known line, such as Chinese hamster ovarian line or *Escherichia coli* line. In this regard, comparing the reference spectrum to the collected spectrum may comprise computing by the processing device, a difference spectrum as the difference between the reference spectrum, such as the spectrum of a Chinese hamster ovarian line or *Escherichia coli* line, and the collected spectrum. Moreover, the collected Raman spectrum may be measured so as to contain sufficient spectral content to examine at least substantially the entirety of the contents of the targeted volume, e.g., a single cell.

According to further aspects of the present disclosure, a system that detects mycoplasma in a manufacturing application, comprises an optical imaging system and a processor. The optical imaging system implements a Raman spectrometer that is controlled to direct a laser to a targeted volume within a sample area so as to collect a Raman spectrum of a single cell of a known cell line of interest. The processor is coupled to the optical imaging system. In this manner, the processor executes program code to receive the Raman spectrum, and to access reference spectra that describes the known line. The reference spectra comprise at least two of: spectral measurements of mycoplasma by itself, a contaminated cell line, and a pure cell line. The processor further executes program code to compare the reference spectra to the collected spectrum, and identify whether there is at least one unnatural molecular composition within the collected spectrum based upon the comparison of the reference spectra to the collected spectrum. Yet further, the processor executes program code to provide an indication as to whether mycoplasma is detected in the collected Raman spectrum based upon whether at least one unnatural molecular composition is identified within the collected spectrum, and stop the manufacturing application where mycoplasma is detected in the collected Raman spectrum.

DETAILED DESCRIPTION

Figure 1:
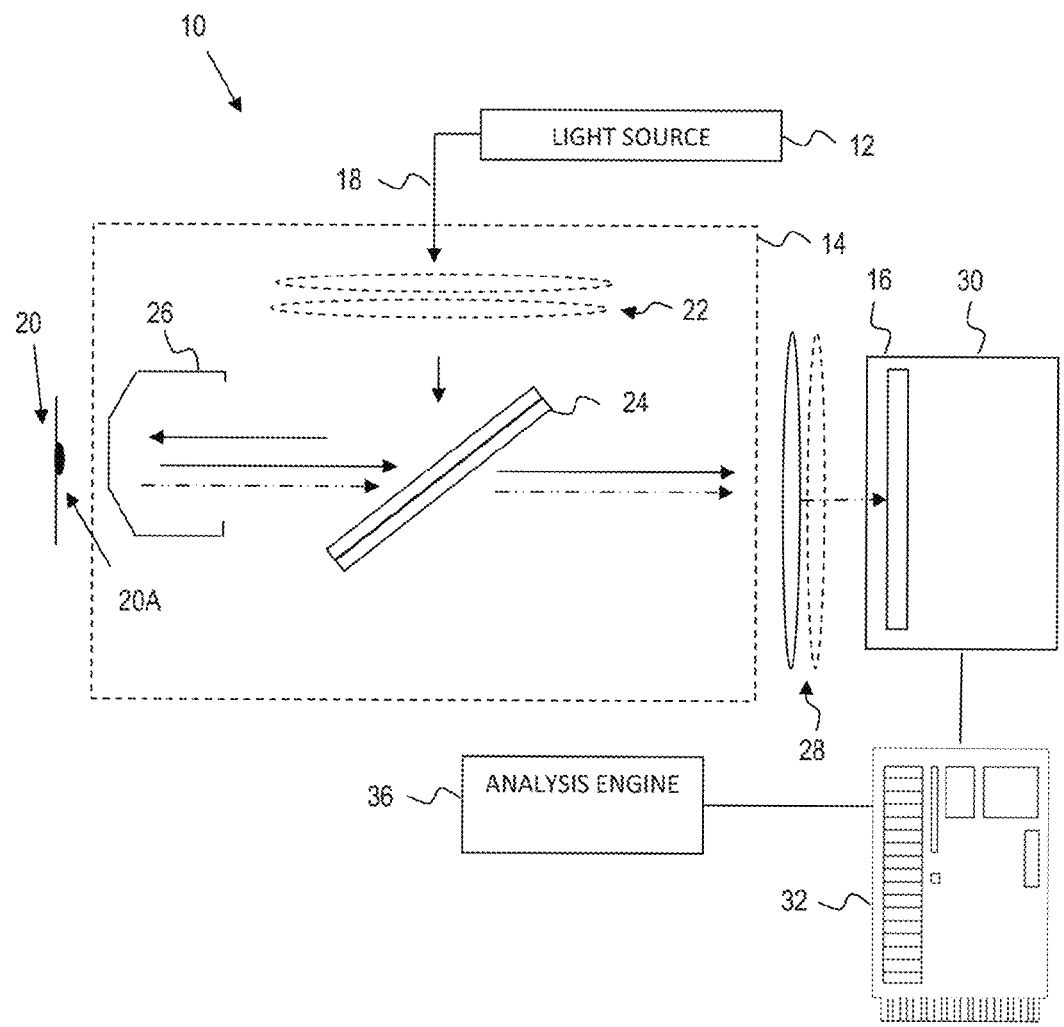
FIG. 1 is a simplified illustration of a Raman spectroscopy system, according to various aspects of the present disclosure.

Many bioprocesses utilize cell cultures. For instance, a bioprocess may utilize hosts cells for the industrial production of recombinant protein pharmaceuticals. By way of illustration, biotechnology in pharmaceutical manufacturing use recombinant technology to modify materials within bacteria, such as *Escherichia coli* (*E. coli*), to produce human insulin. Further, a wide variety of other cell lines are used to contain and serve as a template for the biosynthesis of many new drugs. However, when the cell lines become contaminated, the recombinant process does not yield the correct therapeutic material or drug.

Mycoplasma is a common and difficult to diagnose contaminant of such bioprocess manufacturing applications. For instance, mycoplasmas can contaminate and destroy cell cultures used to catalyze biochemical reactions within microorganisms. Moreover, mycoplasma can persist for long periods of time without apparent cell damage, which can cause challenges in the early detection of the mycoplasma contamination. As such, mycoplasmas are particularly detrimental to industrial bioprocesses, including bioprocesses that utilize host cells for industrial production of recombinant protein pharmaceuticals.

Mycoplasmas do not have cell walls of their own and rely on an association with a host cell to survive. Because mycoplasma exist within another cell, it is difficult to detect the contaminant, even with chemical methods such as ELISA (an antigen-based enzyme-linked immunosorbent assay) or antibody-antigen detection systems.

In addition to *Escherichia coli*, another susceptible cell line to mycoplasma contamination is Chinese hamster ovarian (CHO) cells, which are widely used in bioprocessing to produce complicated proteinaceous drugs. The host CHO cells express recombinant proteins very efficiently and have become the mammalian analog to *Escherichia coli* in the biotechnology industry. When the CHO cells express optimally, they yield very high levels of proteins needed for drug manufacturing.

According to aspects of the present disclosure, Raman spectroscopy is utilized to distinguish and/or otherwise identify host cells that are free from mycoplasma contamination (unmycoplasma contaminated host cells) from mycoplasma contaminated cells in a biotechnology production or research application. Detection of mycoplasma enables processes to be stopped if tested samples indicate that a product is contaminated, saving potentially weeks of process time and expensive reagents.

Detection of mycoplasma in a cell culture can be accomplished according to various aspects of the present disclosure, using an optical imaging system that implements a Raman spectrometer. More particularly, an optical imaging system implements a Raman spectrometer that is controlled by a processor to direct a laser to a targeted volume within a sample area so as to collect a Raman spectrum of a single cell of a known cell line of interest, as will be described in greater detail herein.

Referring now to the drawings, and in particular, to FIG. 1, a simplified Raman system is provided for purposes of clear illustration herein. The Raman system includes an optical imaging system 10 having in general, a light source 12, optics 14 and at least one image output device 16. The light source 12 in the illustrative example comprises a high intensity laser capable of generating a laser beam 18 having a narrow spectral bandwidth. The optics 14 comprise one or more optical components, such as lenses, reflection surfaces, and/or other optical devices necessary to direct the laser beam 18 towards a sample area 20. For instance, as illustrated, the laser beam 18 passes through first optics 22, e.g., one or more optional lenses and/or reflection surfaces, which direct the laser beam 18 towards an optical device 24 such as a long pass dichroic mirror. As illustrated, the laser beam 18 travels along a first optical path as schematically represented by a solid arrow passing through the optics 22.

Light from the laser beam 18 is reflected by the optical device 24 along a second optical path so as to pass the laser beam 18 through an objective 26 as schematically illustrated by the solid arrow pointing from the optical device 24 towards the objective 26. The objective 26 serves to focus the laser beam 18 onto the sample within the sample area 20. For instance, according to various aspects of the present disclosure, the objective 26 may be utilized focus the laser beam 18 onto a single cell located within the sample area 20, as will be described in greater detail herein.

According to various aspects of the present disclosure, the sample area 20 includes a sample collected or otherwise deposited, e.g., from a cell culture, onto an interrogation region 20A, e.g., a sample substrate within the sample area. However, any desired sampling and/or sample preparation techniques may be utilized to collect a suitable sample for interrogation. Regardless of sampling technology, a targeted volume of the sample collected in the interrogation region 20A of the sample area 20 is illuminated by the light source 12.

Scattered and dispersed light is collected from the sample area 20 back through the objective 26 along a third optical path that is generally opposite in direction of the second optical path. In this regard, the interaction between the laser light and the sample collected in the sample area 20 leads to Raman scattering of light that is shifted in wavelength from the light source 12. As such, the light directed along the third optical path includes inelastically scattered photons due to Raman scattering. The inelastically scattered photons are schematically illustrated along the third optical path by the dash dot arrow pointing from the objective 26 towards the optical device 24 to distinguish the Raman scattering from the light (solid arrow pointing from the objective 26 towards the optical device 24) at the wavelength of the laser.

The light along the third optical path is directed by the optical device 24 along a fourth optical path, which is parallel to the third optical path and is seen between the optical device 24 and a filter device 28. In a manner analogous to that set out above, the inelastically scattered photons are schematically illustrated along the fourth optical path by the dash dot arrow to distinguish the Raman scattering from the light (solid arrow) at the wavelength of the laser.

The inelastically scattered photons directed along the fourth optical path are separated from the elastic incident photons, e.g., using at least one appropriate filter device 28, e.g., a longpass filter, a bandpass filter, etc., such that the inelastically scattered photons are passed to a spectrometer 30 and a processing device 32, which implements one or more filters as described in greater detail herein. As such, only the dash dot arrow corresponding to the inelastically scattered photons (and not the solid arrow corresponding to light at the wavelength of the laser) is schematically illustrated as passing from the filter device 28 to the spectrometer 30.

In a non-limiting but illustrative implementation, the spectrometer 30 may include a spectrometer grating that passes the filtered light to the image output device 16, e.g., a two dimensional charge coupled device (CCD) where the divergence in angles of the light exiting the grating causes light at different wavelengths to arrive on different pixels of the CCD to capture spectral data representative of the Raman spectra of the particle under interrogation. Thus, the image output device 16 receives inelastically scattered photons to output information regarding the sample interrogated on the sample substrate.

The Raman spectrum collected from the CCD of the optical output device 16 is collected by the processing device 32 and an analysis engine 36 of the processing device 32 analyzes the collected spectrum to determine whether the collected spectrum suggests that mycoplasma is present in the tested sample.

According to aspects of the present disclosure, the processor is configured to receive the Raman spectrum. The processor is further configured to access a reference spectrum, where the reference spectrum describes a known line of interest via a spectrum that is known to be free of mycoplasma. The processor is still further configured to compare the reference spectrum to the collected spectrum, identify whether there are unnatural molecular compositions within the collected spectrum based upon the comparison of the reference spectrum to the collected spectrum and provide an indication as to whether mycoplasma is detected in the collected spectrum based upon whether unnatural molecular compositions are identified within the collected spectrum.

In an illustrative implementation, the optical imaging system is controlled by the processor to scan the sample area to locate targeted volumes that are suspected of containing a cell of the known cell line of interest. For example, the processor identifies whether the targeted volume contains a cell from a select one of a Chinese hamster ovarian line and *Escherichia coli* line.

As an illustrative example of the above implementation, the processing device 32 directs the laser source 12 to emit a beam 18 that is focused by the objective 26 onto a single cell within the interrogation region 20A of the sample area 20. The processing device 32 then interrogates the sample area at the determined target location to produce interrogation data used by the analysis engine to determine whether the targeted and interrogated cell exhibits characteristics of mycoplasma contamination, as described more fully herein.

In a further illustrative exemplary implementation, the processor of the processing device 32 broadly interrogates the interrogation region 20A of the sample area 20. The processing device then selects from within the interrogated region, one or more specific cells to target for more detailed interrogation. The processing device 32 then directs the laser source 12 to emit a beam 18 that is focused by the objective 26 onto a single selected and targeted cell within the interrogation region 20A of the sample area 20. The processing device 32 then interrogates the sample area at the determined target location to produce interrogation data.

The analysis engine 36 evaluates the specific targeted spectrum to determine whether the targeted and interrogated cell exhibits characteristics of mycoplasma contamination. For instance, in an illustrative implementation, the processor compares the reference spectrum to the collected spectrum by computing a difference spectrum as the difference between the reference spectrum and the collected spectrum. The processor further identifies whether there are unnatural molecular compositions within the collected spectrum based upon the comparison of the reference spectrum to the collected spectrum by identifying unnatural molecules based upon an analysis of the difference spectrum. The processing device 32 can optionally trigger an event such as an alarm or message if mycoplasma is detected.

In this regard, other optics configurations may be implemented within the spirit and scope of the present disclosure. For instance, the optics 14 may utilize various combinations of filters, beam splitters, lenses, mirrors etc. Likewise, the optical output device 16 can be implemented in alternative configurations that are suitable for Raman processing. Moreover, the processing device 32 may utilize a first optical device for general interrogation, and a second optical device for targeting a specific cell within the sample area, etc. Still further, other targeting and/or selection approaches can be utilized to identify the region of the sample area 20 for Raman analysis.

In addition, Raman spectroscopy can be applied using any of the systems and/or processes set out in U.S. Pat. No. 7,532,314, issued May 12, 2009 to Black et al., entitled "Systems and Methods for Biological and Chemical Detection", the disclosure of which is hereby incorporated by reference in its entirety.

Figure 2:
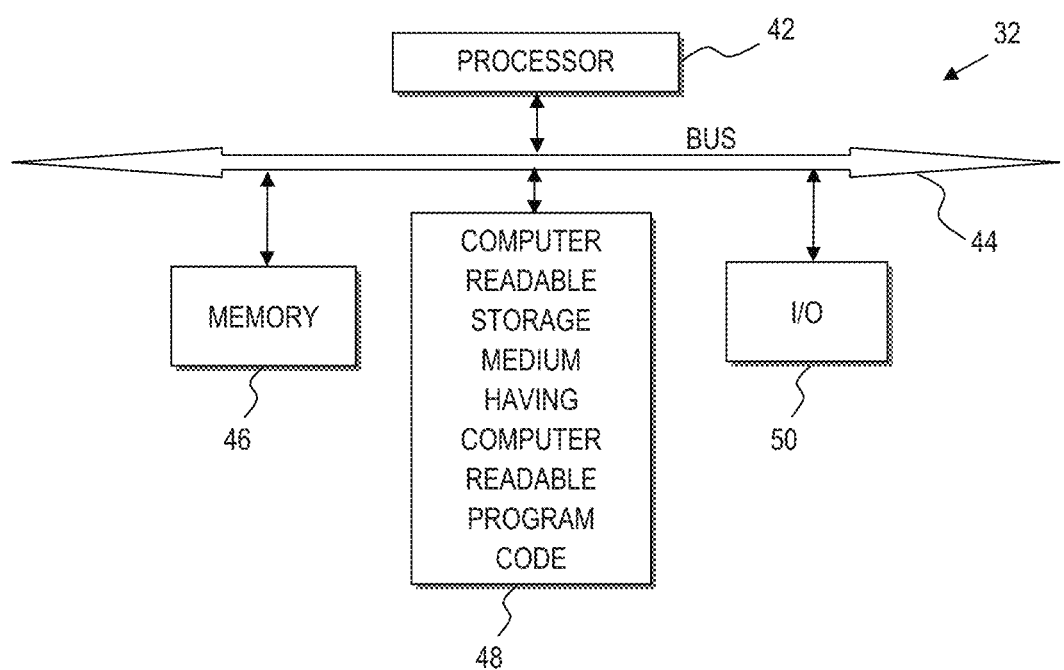
FIG. 2 is a block diagram of a processing device that processes Raman spectral data, e.g., which may be collected from the Raman system of FIG. 1.

Referring to FIG. 2, a block diagram of an exemplary implementation of the processing device 32 is depicted in accordance with various aspects of the present disclosure. The processing device 32 comprises one or more processors 42 connected to system bus 44. Also connected to system bus 44 is memory 48, a computer usable storage medium 48 and one or more input/output devices 50. The computer usable storage medium 48 has computer usable program code embodied thereon, which is executed by the processor 42 to implement any aspect of the present disclosure, for example, to implement the analysis engine 36 and/or any aspect of any of the mycoplasma detection methods described and set out more fully herein.

The architecture and features of the processing device 32 are presented by way of illustration and not by way of limitation. In that regard, the processor 32 may have an alternative architecture and/or features to that described with reference to FIG. 2. Moreover, the processing device 32 need not be physically linked to the optical device 16. Rather, the optical imaging system 10 could collect data that is stored for subsequent processing by the processing device 32, whether integrated with the optical imaging system 10, located off-line, off-site or otherwise, so long as the processing device 32 can implement the filters as described more fully herein.

Recombinant technology can be used to modify materials within bacteria. In this regard, a wide variety of cell lines are used to contain and serve as a template for the biosynthesis of many products. However, when the cell lines become contaminated, the recombinant process does not yield the correct therapeutic material or drug. However, according to aspects of the present disclosure, methods are provided to identify unmycoplasma contaminated host cells from uncontaminated cells.

Figure 3:
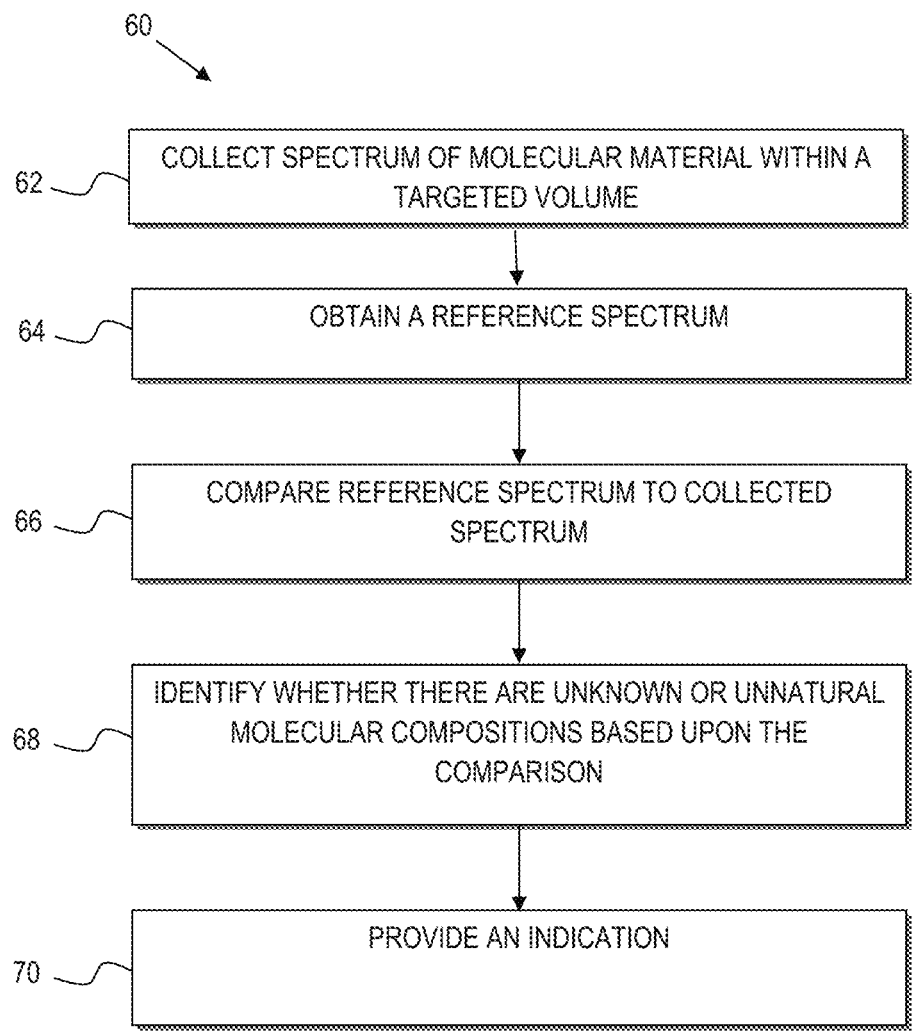
FIG. 3 is a block diagram of a method of detecting mycoplasma according to various aspects of the present disclosure.

Referring to FIG. 3, a method 60 is provided for detecting mycoplasma in a sample. The method comprises collecting a Raman spectrum of a targeted volume within a sample at 62, where the targeted volume contains a known cell line of interest. For instance, the targeted volume may comprise a cell located within an interrogation region 20A of the sample area 20 in the optical imaging system 10 of FIG. 1. By way of illustration, the method 60 may be utilized to inspect a culture in a bioprocess that contains a susceptible cell line such as the Chinese hamster ovarian line of cells or the *Escherichia coli* line of cells. Regardless, the collected Raman spectrum preferably targets a single cell of the corresponding known cell line.

The method further comprises obtaining a reference spectrum uniquely associated with the known cell line at 64 where the obtained reference spectrum is known to be free of mycoplasma contamination. In an illustrative example, the collection of the known spectrum consists of the spectral measurements of mycoplasma by itself, a contaminated cell line and a pure cell line.

The Raman system used to collect the spectrum may be required to scan the sample of interest to identify at least one targeted volume as a potential host for mycoplasma where the targeted volume is identified as a belonging to a known line of interest. The Raman system may alternatively otherwise evaluate regions of the overall sample area to locate and identify a targeted volume that contains a cell from the cell line of interest. As such, the method may perform the collecting of a Raman spectrum of a targeted volume within a sample of interest and identifying the targeted volume as a potential host for mycoplasma if the targeted volume is identified as a belonging to a known line, e.g., Chinese hamster ovarian line of cells or the *Escherichia coli* line of cells, by way of example.

The method still further comprises comparing the reference spectrum 64 to the collected spectrum at 66. In an exemplary implementation, the reference spectrum is compared to the collected spectrum using the processing device 32, and more particularly, the analysis engine 36 of FIG. 1. Particularly, the reference spectrum is compared to the collected spectrum by computing, e.g., by the processing device 32 and/or analysis engine 36, a difference spectrum as the difference between the reference spectrum and the collected spectrum.

The method also comprises identifying whether there are unknown or unnatural molecular compositions within the collected spectrum based upon the comparison of the reference spectrum to the collected spectrum at 68 and providing an indication as to whether mycoplasma is detected in the collected Raman spectrum based upon whether unnatural molecular compositions are identified within the collected spectrum at 70. In this regard, Raman spectroscopy is utilized to identify unmycoplasma contaminated host cells from mycoplasma contaminated cells. As a result, contaminated processes can be stopped, thus saving potentially, weeks of process time.

In an exemplary implementation, an indication as to whether mycoplasma is detected in the collected Raman spectrum is based upon whether unnatural molecular compositions are identified within the collected spectrum. Unnatural molecular compositions can be identified by identifying unnatural molecules based upon an analysis of a difference spectrum computed between the collected spectrum and the reference spectrum.

According to various aspects of the present disclosure, Raman spectroscopy has been developed and used to identify bacteria. The identification is phenomenological and yields a very complex spectral profile that is indicative of the proteinaceous composition of the cell. In this regard, spectral differences exist between cells that are known to be pure and contaminated cells. However, by evaluating a sample, e.g., using the system of FIG. 1 and/or the method of FIG. 3, the early detection of contaminated cell lines can be achieved, thus potentially saving weeks of bioprocess time and money.

According to aspects of the present disclosure, the entire contents of a cell are examined. If a parasitic cell exists, e.g., within a Chinese hamster ovarian host cell or *Escherichia coli* host cell in the examples provided herein, the Raman spectrum looks uniquely different from a non-contaminated cell. Thus, Raman spectroscopy as set out and described more fully herein provides an early diagnostic technique for biotechnology process monitoring.

Figure 4:
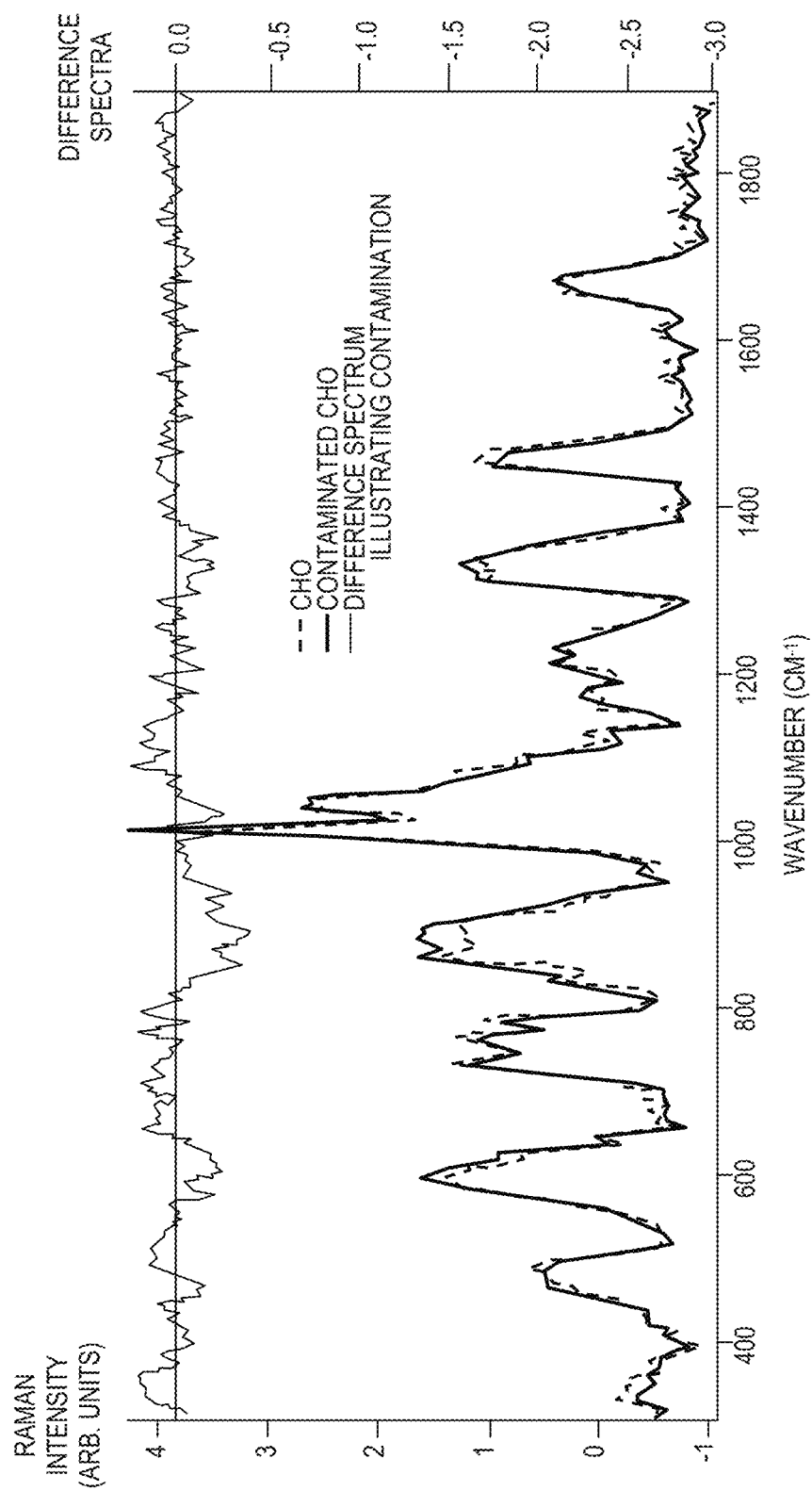
FIG. 4 is a chart illustrating exemplary spectra showing mycoplasma detection of an illustrative sample, according to various aspects of the present disclosure.

Referring to FIG. 4, a sample spectrum is shown. As illustrated, the wavenumber is plotted on the axis of abscissa and Raman intensity is plotted on the axis of the ordinate. A difference measure is plotted on an axis opposite of the Raman intensity. As illustrated in FIG. 4, subtle differences between contaminated and uncontaminated cells are determined. In this regard, the measured spectral information is described as a superposition of all the molecular material detected, e.g., all molecular material illuminated by the laser beam 18 of the laser source 12 in FIG. 1.

In an illustrative bioprocess application, a Chinese ovarian hamster cell is evaluated. The collected spectral information is illustrated with the trace having dots spaced throughout the trace. A known uncontaminated trace, represented by a solid, light gray trace is overlaid with the collected spectrum. The identity of the cultured cell line is known, e.g., the Raman spectral signature of a Chinese hamster ovarian host cell is known or has otherwise been previously determined. Thus, according to various aspects of the present disclosure, a difference spectrum (known spectrum—measured spectrum) illustrates that there are unknown or unnatural molecular compositions within the illuminated volume (cell). The difference spectrum is illustrated as the light solid trace on showing the scale on the right most axis of the ordinate. Notably, if the collected spectrum matched the known spectrum, the difference spectrum would be a substantially horizontal line. However, differences at various spectral positions indicate unnatural molecular compositions within the collected sample. By evaluating this difference signal, information contained therein serves as an indication of whether mycoplasma is present in the sample.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure.

Having thus described the disclosure of the present application in detail and by reference to embodiments thereof, it will be apparent that modifications and variations are possible without departing from the scope of the disclosure defined in the appended claims.

What is claimed is:

1. A method of detecting mycoplasma in a manufacturing application, comprising:
    collecting a sample from a cell culture used by a manufacturing application;
    controlling an optical imaging system implementing a Raman spectrometer to direct a laser to a targeted volume within a sample area so as to collect a Raman spectrum of a single cell of a known cell line of interest;
    receiving, by a processor, the Raman spectrum;
    accessing reference spectra uniquely associated with the known cell line and which describes the known line, the reference spectra comprising at least one of: spectral measurements of mycoplasma by itself, and a contaminated cell line;

comparing, using the processor, the reference spectra to the collected spectrum by computing a difference spectrum from the collected spectrum and a select spectrum of the reference spectra;

identifying whether there is at least one unnatural molecular composition within the collected spectrum based upon the comparison of the reference spectra to the collected spectrum by evaluating differences at select spectral positions of the difference spectrum that indicate unnatural molecular compositions;

providing an indication as to whether mycoplasma is detected in the collected Raman spectrum where at least one unnatural molecular composition is identified within the collected spectrum; and stopping the manufacturing application where mycoplasma is detected in the collected Raman spectrum.

2. The method according to claim 1, wherein:
accessing reference spectra uniquely associated with the known cell line, comprises obtaining the reference spectra comprising all three of spectral measurements of mycoplasma by itself, a contaminated cell line, and a pure cell line.

3. The method according to claim 1, wherein:
stopping the manufacturing application comprises triggering an event including at least one of sounding an alarm and sending a message.

4. The method according to claim 1, wherein:
collecting a sample from a cell culture used by a manufacturing application comprises collecting the sample from a cell culture used by a bioprocess manufacturing application that uses recombinant technology to modify materials within bacteria.

5. The method according to claim 1, wherein:
controlling an optical imaging system implementing a Raman spectrometer to direct a laser to a targeted volume within a sample area so as to collect a Raman spectrum of a single cell of a known cell line of interest further comprises:
utilizing a first optical device for general interrogation, and a second optical device for targeting a specific cell within the sample area.

6. The method according to claim 1, further comprising:
identifying whether the targeted volume contains a cell from a select one of a Chinese hamster ovarian line and *Escherichia coli* line.

7. The method according to claim 1, wherein the targeted volume comprises a single cell.

8. The method according to claim 7, wherein the collected Raman spectrum contains sufficient spectral content to examine at least substantially the entirety of the contents of the cell within the targeted volume.

9. The method according to claim 1, wherein the collected Raman spectrum is a superposition of all the molecular material of a single cell being illuminated by a laser used to collect the Raman spectrum.

10. The method according to claim 1, further comprising:
scanning the sample of interest to identify at least one targeted volume as a potential host for mycoplasma where the targeted volume is identified as a belonging to a known line of interest; and
evaluating at least one targeted volume determined to be a potential host for mycoplasma by:
collecting a Raman spectrum of the targeted volume within a sample under evaluation, the targeted volume containing a known cell line of interest;
comparing, using a processing device, the reference spectra to the collected Raman spectrum;
identifying whether there is at least one unnatural molecular composition within the collected spectrum based upon the comparison of the reference spectra to the collected spectrum; and
providing an indication as to whether mycoplasma is detected in the collected Raman spectrum based upon whether unnatural molecular compositions are identified within the collected spectrum.

11. The method according to claim 1, wherein computing a difference spectrum comprises computing a difference spectrum from the collected spectrum and the contaminated cell line spectrum from the reference spectra.

12. The method according to claim 1, wherein computing a difference spectrum comprises computing a difference spectrum from the collected spectrum and the mycoplasma by itself spectrum from the reference spectra.

13. A system that detects mycoplasma in a manufacturing application, comprising:
an optical imaging system implementing a Raman spectrometer that is controlled to direct a laser to a targeted volume within a sample area so as to collect a Raman spectrum of a single cell of a known cell line of interest;
a processor coupled to the optical imaging system, wherein the processor executes program code to:
receive the Raman spectrum, the processor further configured to access reference spectra that describes the known line, the reference spectra comprising all three of spectral measurements of mycoplasma by itself, a contaminated cell line, and a pure cell line;
compare the reference spectra to the collected spectrum by computing a difference spectrum from the collected spectrum and a select spectrum of the reference spectra;
identify whether there is at least one unnatural molecular composition within the collected spectrum based upon the comparison of the reference spectra to the collected spectrum by evaluating differences at select spectral positions of the difference spectrum that indicate unnatural molecular compositions;
provide an indication as to whether mycoplasma is detected in the collected Raman spectrum based upon whether at least one unnatural molecular composition is identified within the collected spectrum; and
stop the manufacturing application where mycoplasma is detected in the collected Raman spectrum.

14. The system according to claim 13, wherein:
the optical imaging system is controlled by the processor to scan the sample area to locate targeted volumes that are suspected of containing a cell of the known cell line of interest.

15. The system according to claim 13, wherein the processor is further configured to:
identify whether the targeted volume contains a cell from a select one of a Chinese hamster ovarian line and *Escherichia coli* line.

16. The system according to claim 13, wherein:
the processor further executes program code to stop the bioprocess by triggering an event including at least one of sounding an alarm and sending a message.

17. The system according to claim 13, wherein:
the processor further executes program code to control a Raman spectrometer to collect a Raman spectrum of a targeted volume within the sample by:
utilizing a first optical device for general interrogation, and a second optical device for targeting a specific cell within the sample area.

18. The system according to claim 13, wherein the program code for computing a difference spectrum comprises program code for computing a difference spectrum from the collected spectrum and the contaminated cell line spectrum from the reference spectra.

19. The system according to claim 13, wherein the program code for computing a difference spectrum comprises program code for computing a difference spectrum from the collected spectrum and the mycoplasma by itself spectrum from the reference spectra.

\* \* \* \* \*